US008030516B2

(12) United States Patent
Umemoto et al.

(10) Patent No.: US 8,030,516 B2
(45) Date of Patent: Oct. 4, 2011

(54) METHODS FOR PRODUCING PERFLUOROALKANEDI(SULFONYL CHLORIDE)

(75) Inventors: Teruo Umemoto, Denver, CO (US); Norimichi Saito, Denver, CO (US)

(73) Assignee: UBE Industries, Ltd., Tokyo (JP)

( * ) Notice: Subject to any disclaimer, the term of this patent is extended or adjusted under 35 U.S.C. 154(b) by 552 days.

(21) Appl. No.: 12/253,030

(22) Filed: Oct. 16, 2008

(65) Prior Publication Data

US 2009/0105502 A1   Apr. 23, 2009

Related U.S. Application Data

(60) Provisional application No. 60/981,323, filed on Oct. 19, 2007.

(51) Int. Cl.
    *C07C 309/05* (2006.01)
(52) U.S. Cl. ........................................... 562/829
(58) Field of Classification Search ............ None
    See application file for complete search history.

(56) References Cited

U.S. PATENT DOCUMENTS

| | | |
|---|---|---|
| 3,054,661 A | 9/1962 | Muetterties |
| 3,919,204 A | 11/1975 | Boswell, Jr. et al. |
| 4,147,733 A | 4/1979 | Fiske et al. |
| 4,316,906 A | 2/1982 | Ondetti et al. |
| 5,055,223 A | 10/1991 | Reiffenrath et al. |
| 5,093,432 A | 3/1992 | Bierschenk et al. |
| 5,395,916 A | 3/1995 | Mochizuki et al. |
| 5,455,373 A | 10/1995 | Kawa |
| 5,691,081 A | 11/1997 | Krause et al. |
| 5,741,935 A | 4/1998 | Bowden et al. |
| 5,789,580 A | 8/1998 | Chambers et al. |
| 5,824,827 A | 10/1998 | Bildinov et al. |
| 6,222,064 B1 | 4/2001 | Lal et al. |
| 6,737,193 B2 | 5/2004 | Umemoto |
| 6,958,415 B2 | 10/2005 | Lal et al. |
| 7,015,176 B2 | 3/2006 | Bailey, III et al. |
| 7,045,360 B2 | 5/2006 | Shair et al. |
| 7,087,681 B2 | 8/2006 | Umemoto |
| 7,265,247 B1 | 9/2007 | Umemoto et al. |
| 7,381,846 B2 | 6/2008 | Umemoto et al. |
| 7,501,543 B2 | 3/2009 | Umemoto et al. |
| 7,592,491 B2 | 9/2009 | Umemoto |
| 7,820,864 B2 | 10/2010 | Umemoto et al. |
| 7,851,646 B2 | 12/2010 | Umemoto |
| 7,919,635 B2 | 4/2011 | Umemoto |
| 2004/0022720 A1 | 2/2004 | Low et al. |
| 2004/0106827 A1 | 6/2004 | Dolbier et al. |
| 2004/0209854 A1 | 10/2004 | Barkalow et al. |
| 2004/0249209 A1 | 12/2004 | Bailey, III et al. |
| 2005/0012072 A1 | 1/2005 | Bailey, III et al. |
| 2006/0014972 A1 | 1/2006 | Hara et al. |
| 2009/0105502 A1 | 4/2009 | Umemoto et al. |
| 2009/0203924 A1 | 8/2009 | Umemoto et al. |
| 2009/0287024 A1 | 11/2009 | Umemoto et al. |
| 2010/0029992 A1 | 2/2010 | Umemoto et al. |
| 2010/0076215 A9 | 3/2010 | Umemoto et al. |
| 2010/0152463 A1 | 6/2010 | Umemoto et al. |
| 2010/0174096 A1 | 7/2010 | Umemoto et al. |
| 2010/0234605 A1 | 9/2010 | Umemoto et al. |
| 2011/0004022 A1 | 1/2011 | Umemoto |
| 2011/0009672 A1 | 1/2011 | Umemoto |

FOREIGN PATENT DOCUMENTS

| | | |
|---|---|---|
| EP | 0361907 A2 | 4/1990 |
| EP | 1484318 A1 | 12/2004 |
| GB | 227679 | 9/1994 |
| JP | H02-154266 A | 6/1990 |
| JP | 2003-077861 | 4/1991 |
| JP | H07-292050 A | 11/1995 |
| JP | H09-500893 A | 1/1997 |
| JP | 2000-38370 A | 8/2000 |
| JP | 2004-359687 A | 12/2004 |
| JP | 4531852 | 6/2010 |
| TW | 270111 | 2/1996 |
| TW | I 325857 | 6/2010 |
| TW | I 327135 | 7/2010 |
| WO | WO 01/27076 | 4/2001 |
| WO | WO 03/002553 | 1/2003 |
| WO | WO2004/011422 | 2/2004 |
| WO | WO 2008/013550 | 1/2008 |
| WO | WO 2008/014345 | 1/2008 |
| WO | WO 2008/118787 | 10/2008 |
| WO | WO 2009/076345 | 6/2009 |
| WO | WO 2009/114409 | 9/2009 |
| WO | WO 2010/014665 | 2/2010 |
| WO | WO 2010/022001 | 2/2010 |
| WO | WO 2010/033930 | 3/2010 |
| WO | WO 2010/081014 | 7/2010 |

OTHER PUBLICATIONS

Hu et al, Inorganic Chemistry, Synthesis of Perfluoroalkanesulfonyl Halides and Their Sulfonamide Derivatives, 1993, 32, pp. 5007-5010.*

Andrieux et al. (1990) "Outer-sphere and inner-sphere processes in organic chemistry. Reaction of trifluoromethyl bromide with electrochemically generated aromatic anion radicals and sulfur dioxide anion radicals" J. Am. Chem. Soc. 112(2): 786-791.

Calamari and Trask (1979) "Laboratory Explosions" Chemical & Engineering News, 57(19):4.

Des Marteau (1995) "Novel perfluorinated ionomers and ionenes" J. Fluorine Chem. 72(2): 203-208.

Folest et al. (1988) "Electrochemical Synthesis of Trifluoromethane Sulfinic Acid Salt From CF3Br and SO2" Synthetic Communications 18(13): 1491-1494.

Hollitzer and Sartori (1987) "The electrochemical perfluorination (ECPF) of propanesulfonyl fluorides. I: Preparation and ECPF of 1-propanesulfonyl fluoride and 1,3-propanedisulfonyl difluoride" J. Fluorine Chem. 35(2): 329-341.

(Continued)

*Primary Examiner* — Paul A Zucker

(74) *Attorney, Agent, or Firm* — Swanson & Bratschun, L.L.C.

(57) ABSTRACT

Novel methods for preparing perfluoroalkanedi(sulfonyl chloride) are disclosed as are uses for these compounds. In one aspect, a method comprising reacting dibromoperfluoroalkane with $Na_2S_2O_4$ followed by treating with chlorine, an organic compound, and then chlorine to form perfluoroalkanedi(sulfonyl chloride) is provided. Novel perfluoroalkanedi(sulfonyl bromide) compounds are also disclosed.

18 Claims, No Drawings

OTHER PUBLICATIONS

Methods of Organic Chemistry (Houben-Weyl), Work Bench Edition vol. E 10A, Organo-Fluorine Compounds, Gorge Thieme Verlag Stuttgart, New York, 2000 pp. 194-201.

Moss et al. (1995) "Glossary of Class Names of Organic Compounds and Reactive Intermediates Based on Structure" Pure & Appl. Chem, 67(8/9):1307-1375.

Notice of Allowance mailed Oct. 31, 2008 with respect to U.S. Appl. No. 12/106,460.

Notice of Allowance mailed Apr. 29, 2009 with respect to U.S. Appl. No. 12/053,775.

Office Action mailed Jan. 7, 2010 with respect to U.S. Appl. U.S. Appl. No. 12/473,109.

Office Action mailed Oct. 22, 2009 with respect to U.S. Appl. U.S. Appl. No. 12/367,171.

Office Action mailed Nov. 20, 2007 with respect to U.S. Patent No. 7,381,846.

Office Action mailed Dec. 3, 2008 with respect to U.S. Patent No. 7,592,491.

Petrov et al. (2004) "Quadricyclane—thermal cycloaddition to polyfluorinated carbonyl compounds: A simple synthesis of polyfluorinated 3-oxatricyclo[4.2.1.02,5]non-7-enes" Journal of Fluorine Chem. 125(10): 1543-1552.

Qiu and Burton (1993) "A useful synthesis of ω-iodoperfluoroalkanesulfonyl fluorides and perfluoroalkane-α,ω-bis-sulfonyl fluorides" J. Fluorine Chem. 60(1): 93-100.

Tordeux et al. (1990) "Reactions of trifluoromethyl bromide and related halides: part 9. Comparison between additions to carbonyl compounds, enamines, and sulphur dioxide in the presence of zinc" J. Chem. Soc., Perkin Trans. 1 1951-1957.

Xiaobo et al. (1997) "Oxidative Addition and Isomerization Reactions—The Synthesis of cis-ArSF4C1 and trans-ArSF4C1 and cis-PhTeF4C1 and trans-PhTeF4C1", Canadian Journal of Chemistry, 75(12):1878-1884.

Howe-Grant (1995) "Sulfur Hexafluoride" Fluorine Chemistry: A Comprehensive Treatment, John Wiley & Sons, Inc. , New York (ISBN: 0-471-12031-6) pp. 188-195.

Notice of Allowance mailed Oct. 28, 2010 with respect to U.S. Appl. No. 12/367,171.

Notice of Allowance mailed Jun. 23, 2010 with respect to U.S. Appl. No. 12/473,109.

Notice of Allowance mailed Aug. 6, 2010 with respect to U.S. Appl. No. 12/473,129.

Office Action mailed Sep. 13, 2010 with respect to U.S. Application U.S. Appl. No. 12/633,414.

Office Action mailed Mar. 2, 2010 with respect to U.S. Application U.S. Appl. No. 12/473,129.

Sharts and Sheppard (1974) "Modern Methods to Prepare Monofluoroaliphatic Compounds" Organic Chemistry 21:158-173.

Sheppard and Taft (1972) "The Electronic Properties of Di-, Tri-, Tetra-, and Hexacoordinate Sulfur Substituents" Journal Am. Chem. Soc. 94(6)1919-1923.

Uneyama (2006) "Nucleophilic Substitution on Fluoroaromatic Rings" Organofluorine Chemistry, Blackwell Publishing Ltd., Oxford, UK (ISBN-13: 978-14051-2561-1) pp. 101-107.

Bégué and Bonnet-Delpon (2006). "Recent Advances (1995-2005) in Fluorinated Pharmaceuticals Based on Natural Products" Journal of Fluorine Chemistry 127:992-1012.

Bowden et al. (2000). "A New Method for the Synthesis of Aromatic Sulfurpentafluorides and Studies of the Stability of the Sulfurpentafluoride Group in Common Synthetic Transformations" Tetrahedron 56:3399-3408.

Bunnelle et al. (1990). "Difluorination of Esters. Preparation of α, α-Difluoro Ethers" J. Org. Chem. 55(2):768-770.

Cava and Levinson (1985). "Thionation Reactions of Lawesson's Reagents" Tetrahedron 41(22):5061-5087.

Chambers et al. (1996). "Elemental Fluorine. Part 5.[1,2] Reactions of 1,3-Dithiolanes and Thioglycosides With Fluorine-Iodine Mixtures" J. Chem. Soc. Perkin Trans. 1 1941-1944.

Cochran (Mar. 19, 1979). "Laboratory Explosions" Chemical & Engineering News 57(19):4.

Feiring (1979). "Chemistry in Hydrogen Fluoride. 7. A Novel Synthesis of Aryl Trifluoromethyl Ethers" J. Org. Chem. 44(16):2907-2910.

Furuya et al. (2005). "Synthesis of gem-difluorides From Aldehydes Using DFMBA" Journal of Fluorine Chemistry 126:721-725.

Hasek et al. (1960). "The Chemistry of Sulfur Tetrafluoride. II. The Fluorination of Organic Carbonyl Compounds" Journal of American Chem. Soc. 82(3):543-551.

Hayashi et al. (2002). "2,2-Difluoro-1,3-dimethylimidazolidine (DFI). A New Fluorinating Agent" Chem. Commun. 1618-1619.

Henne and Nager (1951). "Trifluoropropyne" J. Am. Chem. Soc. 73(3):1042-1043.

Hoover and Coffman (1964). "Synthesis and Chemistry of Ethynylsulfur Pentafluoride" Journal of Organic Chem. 29:3567-3570.

Huang and Guo (1981). "The Reaction of Arylsulfur Trifluoride With Sterols" Shanghai Institute of Organic Chemistry, ACTA Chimica Sinica 39(1):68.

Kirsch and Bremer (2000). "Nematic Liquid Crystals for Active Matrix Displays: Molecular Design and Synthesis" Angew. Chem. Int. Ed. 39:4216-4235.

Kirsch and Hahn (2005). "Liquid Crystals Based on Hypervalent Sulfur Fluorides: Exploring the Steric Effects of ortho-Fluorine Substituents" Eur. J. of Org. Chem. 3095-3100.

Kobayashi et al.(2004). "Deoxyfluorination of alcohols using N,N-diethyl-α, α-difluoro-(m-methylbenzyl)amine" Tetrahedron 60:6923-6930.

Kuroboshi et al. (1992). "Oxidative Desulfurization-Fluorination of Xanthates. A Convenient Synthesis of Trifluoromethyl Ethers and Difluoro(methylthio)methyl Ethers" Tetrahedron 33(29): 4173-4176.

Kuroboshi and Hiyama (1991). "A Facile Synthesis of Difluoromethylene Compounds by Oxidative Fluorodesulfurization of Dithioacetals Using Tetrabutylammonium Dihydrogentrifluoride and N-Halo Compounds" Synlett 909-910.

Kuroboshi and Hiyama (1992). "A Facile Synthesis of Trifluoromethylamines by Oxidative Desulfurization-Fluorination of Dithiocarbamates" Tetrahedron 33(29):4177-4178.

Kuroboshi and Hiyama (1992). "Oxidative Desulfurization-Fluorination of Methyl Arenedithiocarboxylates. A Convenient Synthesis of Trifluoromethylated Aromatic Compounds" Chemistry Letters 827-830.

Kuroboshi and Hiyama (1994). "A Convenient Synthesis of Perfluoroalkylated Amines by Oxidative Desulfurization-Fluorination" Tetrahedron 35(23):3983-3984.

Kuroboshi and Hiyama (1994). "A Facile Synthesis of α, α-Difluoroalkyl Ethers and Carbonyl Fluoride Acetals by Oxidative Desulfurization-Fluorination" Synlett 251-252.

Lal et al. (1999). "Bis(2-methoxyethyl)aminosulfur trifluoride: a new broad-spectrum deoxofluorinating agent with enhanced thermal stability" Chem. Commun.215-216.

Lal et al. (2000). "Fluorination of Thiocarbonyl Compounds with Bis(2-methoxyethyl)aminosulfur Trifluoride (Deoxo-Fluor Reagent): A Facile Synthesis of gem-Difluorides" J. Org. Chem. 65:4830-4832.

Lee et al. (1989). "One Pot Phase Transfer Synthesis of O-Alkyl, S-Methyl Dithiocarbonates (Xanthates)" Synthetic Communications 19(3&4):547-552.

Ma and Cahard (2007). "Strategies for Nucleophilic, Electrophilic, and Radical Trifluoromethylations" Journal of Fluorine Chemistry 128:975-996.

Mayer and Scheithauer (1985). Carbonsäuren und Carbonsäure-Derivate E5:891-916.

Middleton (1975). "New Fluorinating Reagents. Dialkylaminosulfur Fluorides" Journal of Organic Chem. 40(5):574-578.

Motherwell and Wilkinson (1991). "Observations on the Reaction of Dithioketals with Para-Iodotoluene Difluoride: A Novel Route to gem-Difluoro Compounds" Synlett 191-192.

Olah et al. (1974). "Synthetic Methods and Reactions. I. Selenium Tetrafluoride and Its Pyridine Complex. Convenient Fluorinating Agents for Fluorination of Ketones, Aldehydes, Amides, Alcohols, Carboxylic Acids, and Anhydrides" Journal of American Chem. Soc. 96(3):925-927.

Ou and Janzen (2000). "Oxidative Fluorination of S, Se and Te Compounds" Journal of Fluorine Chem. 101:279-283.

Ou et al. (1997). "Oxidative Addition and Isomerization Reactions. The Synthesis of cis-and trans- ArSF$_4$Cl and cis-and trans-PhTeF$_4$Cl" Can. Journal of Chem. 75:1878-1884.

Pashinnik et al. (2003). "A New Method for the Synthesis of Organosulfur Trifluorides" Synthetic Communications 33(14):2505-2509.

Petrov et al. (2001). "1,1,2,2-Tetrafluoroethyl-N,N-dimethylamine. A New Selective Fluorinating Agent" Journal of Fluorine Chemistry 109:25-31.

Prakash et al. (1993). "Simplified Preparation of α,α-Difluorodiphenlmethanes From Benzophenone 1,3-Dithiolanes With Sulfuryl Choride and Pyridinium Polyhydrogen Fluoride" Synlett 691-693.

Reddy et al. (2005). "gem-Difluorination of 2,2-Diaryl-1,3-dithiolanes by Selectfluor® and Pyridinium Polyhydrogen Fluoride" Chem. Commun. 654-656.

Rozen and Mishani (1993). "Conversion of Esters to α, α-Difluoro Ethers Using Bromine Trifluoride" J. Chem. Soc. Commun. 1761-1762.

Sasson et al. (2003). "Novel Method for Incorporating the CHF$_2$ Group into Organic Molecules Using BrF$_3$" Organic Letters 5(5):769-771.

Scheeren et al. (1973). "A General Procedure for the Conversion of a Carbonyl Group into a Thione Group with Tetraphosphorus Decasulfide" Communications 149-151.

Seergeva and Dolbier (2004). "A New Synthesis of Pentafluorosulfanylbenzene" Organic Letters 6(14):2417-2419.

Sharts and Sheppard (1974). "Modern Methods to Prepare Monofluoroaliphatic Compounds" Organic Chemistry 21:158-173.

Sheppard (1962). "Alkyl- and Arylsulfur Trifluorides" J. Chem. Soc. 84:3058-3063.

Sheppard (1962). "Arylsulfur Pentafluorides" J. Am. Chem. Soc. 84:3064-3072.

Sheppard and Foster (1972). "Pentafluorophenylsulfur(IV) Derivatives" Journal of Fluorine Chemistry 2:53-61.

Shimizu et al. (1995). "Gem-Difluorination of 1,3-Dithiolanes with the Hexafluoropropene-Diethylamine reagent and N-Iodosuccinimide or 1,3-Dibromo-5,5-Dimethylhydantoin" Journal of Fluorine Chemistry 71:9-12.

Simons and Lewis (1938). "The Preparation of Benzotrifluoride" J. Am. Chem. Soc. 60(2):492.

Sipyagin et al. (2001). "Preparation of the First Ortho-Substituted Pentafluorosulfanylbenzenes" Journal of Fluorine Chemistry 112:287-295.

Smith et al. (1960). "Chemistry of Sulfur Tetrafluoride. III. Organoiminosulfur Difluorides" Journal of American Chem. Soc. 82(3):551-555.

Sondej and Katzenellenbogen (1986). "gem-Difluoro Compounds: A Convenient Preparation from Ketones and Aldehydes by Halogen Fluoride Treatment of 1,3-Dithiolanes" J. Org. Chem. 51:3508-3513.

Tarrant et al. (1954). "Fluoroöléfins. V. The Synthesis of 1,1-Difluoro-3-Methylbutadiene" J. Am. Chem. Soc. 76(9): 2343-2345.

Thayer (2006). "Fabulous Fluorine" Chemical & Engineering News 84(23):15-24.

Thayer (2006). "Constructing Life Sciences Compounds" Chemical & Engineering News 84(23):27-32.

Tozer and Herpin (1996). "Methods for the Synthesis of gem-Difluoromethylene Compounds" Tetrahedron 52(26): 8619-8683.

Tullock et al. (1960). "The Chemistry of Sulfur Tetrafluoride. I. The Synthesis of Sulfur Tetrafluoride" Journal of American Chem. Soc. 82(3):539-542.

Winter and Gard (2004). "Synthesis of SF$_5$-benzene (SF$_5$C$_6$H$_5$) by the SF$_5$-halide Method" Journal of Fluorine Chem. 125:549-552.

Yoshiyama and Fuchigami (1992). "Anodic gem-Difluorination of Dithioacetals" Chemistry Letters 1995-1998.

Davis et al (1999) "Efficient Asymmetric Synthesis of β-Fluoro α-Amino Acids" J. Org. Chem. 64:6931-6934.

Huang and Lu (1992) "The Reaction of Perfluoroalkanesylfonyl Halides" Chinese Journal of Chemistry Chapter VII 10(3)268-273.

Huang and Lu (1992) "The Reaction of Perfluoroalkanesylfonyl Halides" Chinese Journal of Chemistry Chapter VIII 10(3)274-277.

Notice of Allowance mailed Dec. 7, 2010 with respect to U.S. Appl. No. 12/367,171.

Office Action mailed Jun. 1, 2011 with respect to U.S. Appl. No. 12/633,414.

Office Action mailed Jan. 21, 2011 with respect to U.S. Appl. No. 12/305,868.

Oae, Shigeru (1977) "Sulfoxides and Sulfilimines" Organic Chemistry of Sulfur, Plenum Press, NY and London, Chapters 8 and 10, pp. 384-589.

Oae, Shigeru (1977) "Sulfoxides and Sulfilimines" Organic Chemistry of Sulfur, Plenum Press, NY and London, Chapter 10, Section 10.3.7, pp. 572-577.

Patai and Rappoport (1994) "Synthesis of Sulphoxides" The Synthesis of Sulphones, Sulphoxides and Cyclic Sulphides, John Wiley & Sons, An Interscience Publication, Chapter 3, pp. 109-158.

Whitham, Gordon H. (1995) "Organosulfur Chemistry" Oxford Chemistry Primers, 33, Oxford Science Publications, Chapter 3, pp. 34-63 (ISBN-13:9780198558996).

* cited by examiner

METHODS FOR PRODUCING PERFLUOROALKANEDI(SULFONYL CHLORIDE)

TECHNICAL FIELD

The invention relates to methods and compositions useful in the preparation of perfluoroalkanedi(sulfonyl chloride).

BACKGROUND OF THE INVENTION

The present invention relates to methods and compositions for the production of perfluoroalkanedi(sulfonyl chlorides), compounds useful in the production of perfluoroalkanedi (sulfonyl fluorides) [see, for example, Journal of Fluorine Chemistry, Vol. 60 (1993), p.p. 93-100]. Perfluoroalkanedi (sulfonyl fluorides) are important intermediate compounds in the preparation of cycloperfluoroalkanedi(sulfonyl)imide lithium salts, used as electrolytes for lithium secondary batteries [see, for example, Journal of Fluorine Chemistry, Vol. 125 (2004), p.p. 243-252, and U.S. Pat. No. 5,691,081]. Perfluoroalkanedi(sulfonyl fluorides) can also be used in the preparation of perfluorinated ionomers and ionene polymers, each having perfluoroalkanesulfonylimide units, useful as electrochemical materials [see Journal of Fluorine Chemistry, Vol. 72 (1995), p.p. 203-208].

Conventional production of perfluoroalkanedi(sulfonyl chlorides) has proven difficult, especially production of perfluoroalkanedi(sulfonyl chlorides) having the necessary purity and quality to be used in production of highly pure, substantially hydrogen atom-free perfluoroalkanedi(sulfonyl fluoride) compounds. Hydrogen atom-free perfluoro compounds are of great industrial importance, as perfluoro compounds that include hydrogen atoms generally show a decrease in potential life time and other performance related functions, especially when used in batteries and other electronic-based devices.

Conventionally, perfluoroalkanedi(sulfonyl fluorides) are produced using one of the following synthetic methods: (1) Alkanedi(sulfonic acid) is converted to alkanedi(sulfonyl chloride), which is then fluorinated with KF to give alkanedi (sulfonyl fluoride). The alkanedi(sulfonyl fluoride) is electrolyzed in anhydrous hydrogen fluoride to give perfluoroalkanedi(sulfonyl fluoride) [see Journal of Fluorine Chemistry, Vol. 35 (1987), p.p. 329-341]; or (2) Diiodoperfluoroalkane is reacted with $Na_2S_2O_4$, followed by treatment with chlorine to give perfluoroalkanedi(sulfonyl chloride), which is then reacted with KF to give perfluoroalkanedi(sulfonyl fluoride) [see Journal of Fluorine Chemistry, Vol. 60 (1993), p.p. 93-100].

However, each of the above synthetic production methods has one or more significant drawbacks, for example, synthetic method (1) requires electrolysis in anhydrous hydrogen fluoride, of which production efficiency and yield are low. In addition, the expected product, perfluoroalkanedi(sulfonyl fluoride), is accompanied by many intermediately fluorinated alkanedi(sulfonyl fluorides) by-products [see Journal of Fluorine Chemistry, Vol. 35 (1987), p.p. 329-341]. Therefore, the resulting purity of the product is low, requiring additional purification procedures (resulting in enhanced costs and further reduced yields). Synthetic production method (2), on the other hand, requires use of an expensive reactant, diiodoperfluoroalkane. The extra cost makes large scale production of product using method (2) very ineffective. In addition, both of these conventional methods fail to realize highly pure, hydrogen atom-free perfluoroalkaniedi(sulfonyl fluorides) as a product, as these methods inherently result in products having some level of hydrogen atom contamination. In particular, perfluoro compounds prepared by conventional methods contain at minimum several parts per million (ppm) or more of hydrogen atoms, a level that may severely diminish the materials usefulness.

Technology has recently been developed making possible complete perfluorination of organic compounds [see Methods of Organic Chemistry (Houben-Weyl), Work Bench Edition Vol. E 10a, Organo-Fluorine Compounds, Gorge Thieme Verlag Stuttgart, New York, 2000, p.p. 194~201]. This new technology uses molecular fluorine ($F_2$) in the presence of a solvent, which can provide highly pure, virtually hydrogen atom-free $BrCF_2(CF_2)_nCF_2Br$. The level of residual hydrogen atoms remaining on the perfluoro organic compounds synthesized by the method reaches concentrations of below 3 parts per billion (ppb). However, no method for transformation of the $BrCF_2(CF_2)_nCF_2Br$ to the perfluoroalkanedi(sulfonyl chlorides) has been developed.

The present invention is directed toward overcoming one or more of the problems discussed above.

SUMMARY OF THE INVENTION

The present invention provides novel methods and compositions for preparation of perfluoroalkanedi(sulfonyl chloride). In one aspect, a method for preparing perfluoroalkanedi (sulfonyl chloride) is provided, the perfluoroalkanedi (sulfonyl chloride) having a formula (I) as follows:

$$ClSO_2CF_2(CF_2)_nCF_2SO_2Cl \quad (I)$$

In one embodiment the method comprises a first step of reacting a dibromoperfluoroalkane having a formula (II):

$$BrCF_2(CF_2)_nCF_2Br \quad (II)$$

with $SO_2$ radical anion ($SO_2.^-$) or a source of $SO_2$ radical anion; and a second step of reacting the obtained reaction mixture with a halogen selected from a group consisting of chlorine ($Cl_2$), bromine ($Br_2$), and interhalogen compounds consisting of chlorine atom and bromine atom, to form a perfluoroalkanedi(sulfonyl halide) having a formula (III):

$$XSO_2CF_2(F_2)CF_2SO_2X' \quad (III)$$

Step three then provides reacting the obtained perfluoroalkanedi(sulfonyl halide) with an organic compound to form a perfluoroalkanedi(sulfinate) having a formula (IV):

$$MO_2SCF_2(CF_2)_nCF_2SO_2M \quad (IV)$$

Finally, in step four the perfluoroalkanedi(sulfinate) is reacted with chlorine ($Cl_2$) to form perfluoroalkanedi(sulfonyl chloride).

The present invention also provides perfluoroalkanedi(sulfonyl bromide) having a formula (V);

$$BrSO_2CF_2(CF_2)_nCF_2SO_2Br \quad (V)$$

For purposes of the above embodiment, n is a whole number from one to eight, X and X' are independently a bromine atom or a chlorine atom, and M is a hydrogen atom, a metal atom, an ammonium moiety, or a phosphonium moiety.

These and various other features as well as advantages which characterize the invention will be apparent from a reading of the following detailed description and a review of the appended claims.

DETAILED DESCRIPTION OF THE INVENTION

Embodiments of the present invention provide methods and compositions for producing perfluoroalkanedi(sulfonyl chlorides), as represented by formula (I). In some embodiments these methods are useful at an industrial scale, providing high yield and high purity product using low cost reagents. In addition, embodiments of the invention provide convenient phase separation based isolation methods for use in the production of the perfluoroalkanedi(sulfonyl chlorides). Phase separation being useful in industrial scale procedures especially where time and cost are of concern.

Perfluoroalkanedi(sulfonyl chlorides) produced by this invention can be used, for among other things, as intermediates in the preparation of perfluoroalkanedi(sulfonyl fluorides), which can be further derived to cycloperfluoroalkanedi(sulfonyl)imide salts or perfluorinated ionomers and ionene polymers having perfluoroalkanesulfonylimide units. These compounds are particularly useful as electrolytes for long-lived batteries or other like devices.

A distinction from production methods in the prior art is that processes of the invention utilize relatively low cost reagents to provide excellent yields of high purity compounds. Embodiments of the present invention utilize the highly pure $BrCF_2(CF_2)_nCF_2Br$, although other like starting materials may be used. The prepared perfluoroalkanedi(sulfonyl chlorides) can be therefore substantially hydrogen atom-free, having particular usefulness as intermediates in the preparation of electrolytes for batteries (especially lithium batteries) or other devices that require long-acting life spans.

Embodiments of the invention include processes which comprise a first step of reacting a dibromoperfluoroalkane having a formula (II) with a $SO_2$ radical anion ($SO_2.^-$) or a source of $SO_2$ radical anion; in a second step reacting the obtained reaction mixture with a halogen selected from a group consisting of chlorine ($Cl_2$), bromine ($Br_2$), and/or interhalogen compounds consisting of chlorine atom and bromine atom (or mixtures of any of the group members), to form a perfluoroalkanedi(sulfonyl halide) having a formula (III); next, a third step of reacting the obtained perfluoroalkanedi(sulfonyl halide) with an organic compound to form a perfluoroalkanedi(sulfinate) having a formula (IV); and finally in a fourth step, reacting the perfluoroalkanedi(sulfinate) with chlorine ($Cl_2$) to form perfluoroalkanedi(sulfonyl chloride), having a formula (I).

In one embodiment, the processes of the invention have the general reaction scheme as shown in scheme 1:

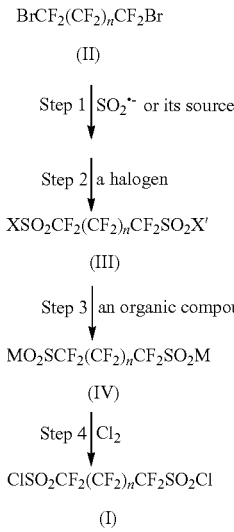

Scheme 1: (Steps 1, 2, 3, and 4)

With regard to the compounds represented by formulas (I), (II), (III), and (IV): n=1~8, X=Br or Cl, X'=Br or Cl, and M=a hydrogen atom, a metal atom, an ammonium moiety, or a phosphonium moiety.

Embodiments of the present invention provide perfluoroalkanedi(sulfonyl bromide) having a formula (V). The perfluoroalkanedi(sulfonyl bromide) is novel intermediate compounds for use in embodiments of the present invention, that is, a main product obtained by steps 1 and 2. The perfluoroalkanedi(sulfonyl bromide) may be represented by the formula (III) having X=X'=Br.

Table 1 provides structure names and formulas for reference when reviewing Scheme 1 and the text that follows:

TABLE 1

Formulas (I~V)

| Name | Structure/Formula Number |
|---|---|
| Perfluoroalkanedi(sulfonyl chloride) | $ClSO_2CF_2(CF_2)_nCF_2SO_2Cl$ (I) |
| Dibromoperfluoroalkane | $BrCF_2(CF_2)_nCF_2Br$ (II) |
| Perfluoroalkanedi(sulfonyl halide) | $XSO_2CF_2(CF_2)_nCF_2SO_2X'$ (III) |
| Perfluoroalkanedi(sulfinate) | $MO_2SCF_2(CF_2)_nCF_2SO_2M$ (IV) |
| Perfluoroalkanedi(sulfonyl bromide) | $BrSO_2CF_2(CF_2)_nCF_2SO_2Br$ (V) |

In more detail, Scheme 1 is represented generally by the following four steps:

Step 1 (Scheme 1)

In embodiments of the invention, step 1 includes reacting a dibromoperfluoroalkane having a formula (II) with $SO_2$ radical anion, or its source, to give a reaction mixture which is used in Step 2. The reaction mixture comprises perfluoroalkaniedi(sulfinate) represented by formula (IV) and bromide anion.

Illustrative dibromoperfluoroalkanes of the invention, as represented by formula (II), include $BrCF_2CF_2CF_2Br$, $BrCF_2(CF_2)_2CF_2Br$, $BrCF_2(CF_2)_3CF_2Br$, $BrCF_2(CF_2)_4CF_2Br$, $BrCF_2(CF_2)_5CF_2Br$, $BrCF_2(CF_2)_6CF_2Br$, $BrCF_2(CF_2)_7CF_2Br$, and $BrCF_2(CF_2)_8CF_2Br$. Each illustrative compound above is commercially available from, for example, Exfluor Corporation (Texas, USA) or can be prepared according to the methods described in U.S. Pat. No. 5,093,432 and/or U.S. Pat. No. 5,455,373, each of which is incorporated by reference in their entirety for all purposes. Note that in some limited circumstances the dibromoperfluoroalkane of formula (II) is a mixture of two or more of $BrCF_2CF_2CF_2Br$, $BrCF_2(CF_2)_2CF_2Br$, $BrCF_2(CF_2)_3CF_2Br$, $BrCF_2(CF_2)_4CF_2Br$, $BrCF_2(CF_2)_5CF_2Br$, $BrCF_2(CF_2)_6CF_2Br$, $BrCF_2(CF_2)_7CF_2Br$, and $BrCF_2(CF_2)_8CF_2Br$.

$SO_2$ radical anions ($SO_2.^-$) for use in the processes described herein can be prepared by reacting a metal and sulfur dioxide ($SO_2$) in a solvent (see Journal of Chemical Society, Perkin Transaction 1, 1990, p.p. 1951-1957). In one embodiment the metal is zinc powder and the solvent is a polar solvent, such as N,N-dimethylformamide, N-methylformamide, formamide, N,N-dimethylacetamide, dimethylsulfoxide, or N-methylpyrrolidinone. In order to obtain product at a good yield, $SO_2$ radical anions are preferably generated in the presence of dibromoperfluoroalkane. The $SO_2$ radical anions can also be generated using electrochemical means as reported in Synthetic Communications, Vol. 18 (1988), p.p. 1491-1494, and Journal of American Chemical Society, Vol. 112 (1990), p.p. 786-791, each of which is incorporated by reference herein in their entirety.

Sources of $SO_2$ radical anions are exemplified as follows: dithionites (hydrosulfites) such as sodium dithionite (sodium hydrosulfite) $Na_2S_2O_4$; this is also expressed as $NaO_2SSO_2Na$), potassium dithionite (potassium hydrosulfite), lithium dithionite (lithium hydrosulfite), ammonium dithionite (ammonium hydrosulfite), and their hydrates; hydroxymethanesulfinates such as hydroxymethanesulfinic acid monosodium salt ($HOCH_2SO_2Na$) and its hydrate such as dihydrate ($HOCH_2SO_2Na.2H_2O$); hydrogen sulfites such as sodium hydrogen sulfite ($NaHSO_3$), potassium hydrogen sulfite, ammonium hydrogen sulfite, and their hydrates; sulfites such as sodium sulfite ($Na_2SO_3$), potassium sulfite, ammonium sulfite, and their hydrates; and a mixture of formic acid and sodium hydrogen sulfite or sodium sulfite. Preferred sources of $SO_2$ radical anions include $Na_2S_2O_4$.

In another embodiment, step one is performed using $Na_2S_2O_4$ as a source of the $SO_2$ radical anion in the presence of a base, since a base will neutralize $SO_2$ generated as a by-product of the reaction. Examples of bases for use in this manner include carbonates such as sodium carbonate, sodium hydrogencarbonate, potassium carbonate, potassium hydrogencarbonate, lithium carbonate, lithium hydrogencarbonate, and so on; phosphates such as sodium phosphate monobasic ($NaH_2PO_4$), sodium phosphate dibasic $Na_2HPO_4$), sodium phosphate tribasic ($Na_3PO_4$), potassium phosphate monobasic ($KH_2PO_4$), potassium phosphate dibasic ($K_2HPO_4$), potassium phosphate tribasic ($K_3PO_4$), lithium phosphate monobasic ($LiH_2PO_4$), lithium phosphate dibasic ($Li_2HPO_4$), lithium phosphate tribasic ($Li_3PO_4$), and so on; hydroxides such as sodium hydroxide, potassium hydroxide, lithium hydroxide, and so on; amines such as ammonia, methylamine, dimethylamine, trimethylamine, ethylamine, diethylamine, triethylamine, propylamine, pyridine, methylpyridine, dimethylpyridine, trimethylpyridine, and so on; and carboxylates such as sodium acetate, potassium acetate, and so on. In general the carbonates and phosphates are preferable in this manner.

In another embodiment, step one is performed using $Na_2S_2O_4$ (source of the $SO_2$ radical anion) and $NaHCO_3$ (a base), which can be expressed by equation one (Eq. 1). Therefore, the resulting reaction products are generally $NaO_2SCF_2$ $(CF_2)_nCF_2SO_2Na$, $NaBr$, $NaHSO_3$, and $CO_2$. In typical situations most of the $CO_2$ is removed from the reaction mixture via gas evolution.

$$BrCF_2(CF_2)_nCF_2Br+2Na_2S_2O_4+2NaHCO_3+ \\ 2H_2O \rightarrow NaO_2SCF_2(CF_2)_nCF_2SO_2Na+2NaBr+ \\ 2NaHSO_3+2CO_2 \quad (Eq\ 1)$$

In other embodiments of the invention, step one is carried out in a solvent. From the viewpoint of reaction efficiency and yield, the reaction of step one is preferably carried out in the presence of one or more solvents. The solvent is preferably a polar solvent, and more preferably a polar solvent that does not substantially react with the starting material(s) and reagents, the intermediates, and/or the final product(s). Suitable solvents for use herein include, but are not limited to, water; nitriles such as acetonitrile, propionitrile, butyronitrile, and so on; amides such as N,N-dimethylformamide, N,N-dimethylacetamide, N-methylformamide, N-methyacetamide, formamide, pyrrolidinone, N-methylpyrrolidinone, and so on; alcohols such as methanol, ethanol, propanol, isopropanol, butanol, isobutanol, sec-butanol, tert-butanol, and so on; nitro compounds such as nitromethane, nitroethane, nitropropane, and so on; carbonates such as dimethyl carbonate, diethyl carbonate, ethyl methyl carbonate, ethylene carbonate, propylene carbonate, and so on; lactones such as propiolactone, butyrolactone, and so on; ethers such as diethyl ether, dipropyl ether, di(isopropyl)ether, dibutyl ether, tert-butyl methyl ether, tetrahydrofuran, dioxane, and so on; as well as mixtures of the above. In some embodiments the solvent is a mixture of water and a nitrile or a mixture of water and an amide. In other enumerated embodiments the solvent is a mixture of water and a nitrile, where a mixture of water and acetonitrile is preferable in that it provides easy phase separation and the benefit that acetonitrile is easily removed from the solution of the reaction mixture by distillation as it has a low boiling point. The removal of acetonitrile (when used) is preferred for step two of synthesis scheme 1.

In order to get a good product yield, the preferable amount of solvent can be chosen in the range of about 0.1 L to about 10 L per 1 mol of the dibromoperfluoroalkane used. About 0.2 L to about 5 L of solvent is more preferable. When a mixture of two solvents is used, it is preferable that the ratio can be chosen in the range of about 5:95 to about 95:5, and more preferably in the range of about 1:9 to about 9:1.

In order to obtain good product yields in step one, the reaction temperature is in the range of about $-60°$ C.~$+150°$ C. More preferably, the reaction temperature is about $-20°$ C.~$+100°$ C. and is some cases in the range of about $0°$ C.~$+80°$ C.

In order to obtain good product yields in step one, the amount of $SO_2$ radical anions is about 2 mole or more for every one mole of dibromoperfluoroalkane (formula II) present. Preferably, about 2 to about 5 moles of the $SO_2$ radical anions can be used, and more preferably about 2 to about 3 moles can be used, especially where cost is a concern. When a source of $SO_2$ radical anion is used and the source provides 1 mole from n moles of the source, the amount of the source used for the reaction is about 2 n mole and more against 1 mole of dibromoperfluoroalkane (formula II). Preferable about 2 n to about 5 n moles of the source can be used, and more preferable about 2 n to about 3 n moles can be used, especially when cost considerations are prevalent.

Note that the reaction time(s) for step one varies dependent upon reaction temperature, and the types and amounts of substrates, reagents, and solvents present. As such, reaction time is generally determined as the amount of time required to complete a particular reaction.

An additional preferable embodiment of step one is that, after the reaction of $BrCF_2(CF_2)_nCF_2Br$ and a $SO_2$ radical anion or its source in a solvent mixture of acetonitrile and water is finished, the water or aqueous layer (lower layer, water layer and aqueous layers used interchangeable herein) is separated from the organic (acetonitrile) layer (upper layer). The separated aqueous or water layer is concentrated to remove at least some acetonitrile contained in the aqueous layer. It is more preferable to remove as much acetonitrile as possible from the aqueous layer. The resulting aqueous layer is then used in step two of synthesis scheme 1. Regardless, for embodiments described above, the aqueous layer of the reaction is used as the starting point for Step 2 (Scheme 1).

Step 2 (Scheme 1)

Embodiments of the invention include a step two: reacting the reaction mixture obtained through step one with a halogen selected from a group consisting of chlorine ($Cl_2$), bromine ($Br_2$), and interhalogen compounds consisting of chlorine atom and bromine atom, to form a perfluoroalkanedi(sulfonyl halide) having a formula (III) (see Scheme 1). Note that in limited cases the halogen can be a mixture of $Cl_2$ and $Br_2$ and/or interhalogens compound. Examples of interhalogen compounds consisting of chlorine atom and bromine atom of the invention include $BrCl$ and $BrCl_3$. A preferable halogen used in step two is chlorine ($Cl_2$) because of cost.

In some embodiments of step two, the reactions are carried out in a solvent, as the reaction can efficiently take place in a solvent. Preferable solvents will not substantially react with the starting materials and/or reagents, the intermediates, or the final products.

Suitable solvents for use herein include, but are not limited to, water; nitriles such as acetonitrile, propionitrile, butyronitrile, and so on; ethers such as diethyl ether, dipropyl ether, di(isopropyl)ether, dibutyl ether, tert-butyl methyl ether, tetrahydrofuran, dioxane, and so on; hydrocarbons such as pentane, hexane, heptane, octane, and so on; halocarbons such as dichloromethane, chloroform, carbon tetrachloride, dichloroethane, trichloroethane, trichlorotrifluoroethane, and so on; esters such as methyl acetate, ethyl acetate, methyl propionate, and so on; and mixtures of any two or more of the above. Water, a mixture of water and a halocarbon, and a mixture of water and a hydrocarbon are preferable solvents for the reaction of step two. These solvents typically provide higher product yield. Also note that water or a mixture of water and a halocarbon are more preferable when easy phase separation, and therefore cost and yield are taken into consideration.

In order to get a good product yield, the preferable amount of solvent can be chosen in the range of about 0.1 L to about 10 L per 1 mol of perfluoroalkanedi(sulfinate) (formula IV) present. About 0.2 L to about 5 L of solvent is more preferable. When a mixture of two solvents is used, it is preferable that the ratio can be chosen in the range of about 5:95 to about 95:5, and more preferably in the range of about 9:1 to about 1:9. When the aqueous layer obtained in step 1 is used, no additional solvent is needed or some solvent may be added in order to be a suitable concentration of the perfluoroalkanedi (sulfinate) mentioned above.

In order to optimize yield with regard to step two, the reaction temperature is selected in the range of from about −30° C. to about +100° C. More typically, the reaction temperature is selected in the range of from about −20° C. to about +70° C. Most typically, the reaction temperature is selected in the range of from about −10° C. to about +50° C.

The amount of halogen used in step two is typically about 2 moles or more per mole of dibromoperfluoroalkane (formula II) used in step one. Since the halogen can react with many products obtained in step one, as well as with the starting materials, such as $Na_2S_2O_4$ used in step one, the amount of the halogen used in step two varies. Therefore, the amount is generally determined as the amount of halogen required to complete the reaction, i.e., the halogen is used in excess.

As described for step one, reaction times for step two vary dependent on reaction temperature, substrate type, reagent type, solvent type, and amounts used of each component. Therefore, reaction time is modified by reaction conditions.

In one preferred embodiment of step two, after a halogen is introduced to the aqueous solution (aqueous or water layer) obtained by Step 1, an organic solvent is added into the reaction mixture, the resulting mixture was stirred or mixed and then allowed to stand, the resulting organic layer then separated from the aqueous layer. The obtained organic layer is then used in step three. When a mixture of water and an organic solvent is used in the reaction of step two, after a halogen is introduced to the reaction mixture of water and the organic solvent, an organic layer is separated from the aqueous layer. The obtained organic layer is used in step three. The suitable organic solvents immiscible with water can be chosen from the examples (except water) shown above. Among them, halocarbons and hydrocarbons are preferable, and halocarbons are more preferable when easy phase separation, and therefore cost and yields are taken into consideration.

Perfluoroalkanedi(sulfonyl bromide) having a formula (V) is novel intermediate compounds for use in embodiments of the present invention. The perfluoroalkanedi(sulfonyl bromides) are prepared using Steps 1 and 2 of Scheme 1 as shown in Eqs. 2 and 3:

(Eq. 2)

Step 1

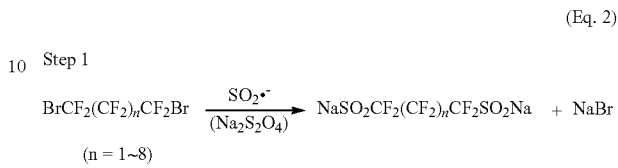

(Eq 3)

Step 2

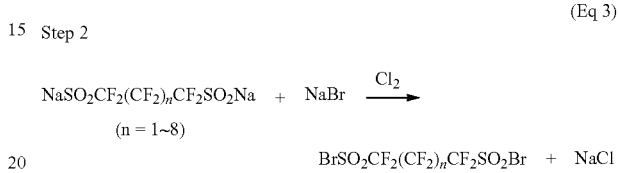

For example, in step 1 (Eq. 2), 1,3-dibromoperfluoropropane reacts with $Na_2S_2O_4$ to give a mixture of sodium perfluoropropanedi(sulfinate) and sodium bromide. In step 2 (Eq. 3), the mixture was treated with chlorine ($Cl_2$), forming perfluoroalkanedi(sulfonyl bromide) (formula V). In step 2, chlorine reacts with bromide anion such as NaBr to give $Br_2$, which reacts with sodium perfluoroalkanedi(sulfinate) to give perfluoroalkanedi(sulfonyl bromide). This is demonstrated in Examples 3 and 5 (mentioned below) where treatment of sodium perfluoropropane-1,3-di(sulfinate) and sodium perfluorobutane-1,4-di(sulfinate) with bromine ($Br_2$) produced perfluoropropane-1,3-di(sulfonyl bromide) (formula V, n=1) and perfluorobutane-1,4-di(sulfonyl bromide) (formula V, n=2) in 94% and 98% yield, respectively, as shown in Eqs. 4 and 5.

(Eq 4)

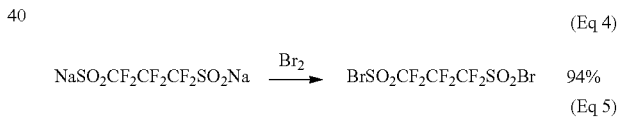

(Eq 5)

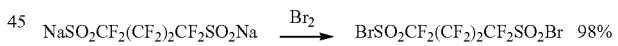

Step 3 (Scheme 1)

Embodiments of the invention include a third step: reacting the obtained perfluoroalkanedi(sulfonyl halide) with an organic compound to form a perfluoroalkanedi(sulfinate), as represented by formula (IV).

Organic compounds of the invention used herein, are typically selected from compounds that form C—Br and/or C—Cl bonds by reaction with the perfluoroalkanedi(sulfonyl halides) of formula (III).

Preferable examples of organic compounds of the invention include: ketones such as acetone, methyl ethyl ketone, diethyl ketone, dipropyl ketone, dibutyl ketone, methyl butyl ketone, dipentyl ketone, dihexyl ketone, diheptyl ketone, dioctyl ketone, dinonyl ketone, didecyl ketone, methyl octyl ketone, cyclobutanone, cyclopentanone, cycloheptanone, cyclooctanone, methylcyclohexanone, dimethycyclohexanone, butylcyclohexanone, and so on; aldehydes such as acetoaldehyde, propioaldehyde, butyroaldehyde, and so on; diketones such as 2,4-pentanedione, 2,3-pentanedione, 2,4-hexanedione, 2,4-heptanedione, cyclopentane-1,2-dione, cyclopentane-1,3-dione, cyclohexane-1,2-dione, cyclohexane-1,3-dione, cyclohexane-1,4-dione, cycloheptane-1,3-dione, cyclooctane-1,3-dione, and so on; ketoaldehydes such as 2-oxo-1-propioaldehyde, 3-oxo-1-butyroaldehyde, 3-oxo-1-hexanal, and so on; ketoesters such as methyl acetoacetate, ethyl acetoacetate, methyl 3-oxo-butyrate, methyl cyclopentanone-1-carboxylate, methyl cyclohexanone-1-carboxylate, and so on; phenols (phenol and its derivatives) such as phenol, alkylphenols such as each isomer (o, m, and p-isomers) of methylphenol (cresol), each isomer of dimethylphenol, each isomer of trimethylphenol, each isomer of ethylphenol, each isomer of n-propylphenol, each isomer of isopropylphenol, each isomer of a-butylphenol, each isomer of sec-butylphenyl, each isomer of isobutylphenol, each isomer of tert-butylphenol and so on, halophenols such as each isomer of chlorophenol, each isomer of bromophenol, and so on, alkyl (halo)phenols such as each isomer of bromo(methyl)phenol, each isomer of chloro(methyl)phenol, each isomer of bromo (ethyl)phenol, each isomer of chloro(ethyl)isomer, each isomer of bromo(propylphenol, each isomer of bromo(tert-butyl)phenol, each isomer of chloro(tert-butyl)phenol, and so on; naphthols such as each isomer of naphthol, each isomer of methylnaphthol, each isomer of dimethylnaphthol, and so on; nitro compounds such as nitromethane, nitroethane, nitropropane, and so on; anilines such as aniline, N-methylaniline, N,N-dimethylaniline, and so on; salts of the organic compounds shown above such as metal salts, ammonium salts, phosphonium salts, and so on.

Preferable examples of metal atoms of the metal salts are alkali metal atoms (Li, Na, Ka, Rb, Cs), alkali earth metal atoms (Be, Mg, Ca, Sr, Ba), transition metal atoms, and so on. Preferable examples of ammonium moieties of ammonium salts of organic compounds are ammonium ($NH_4$), methylammonium, dimethylammonium, trimethylammonium, tetramethylammonium, ethylammonium, diethylammonium, triethylammonium, tetraethylammonium, benzyltrimethylammonium, tetrapropylammonium, tetrabutylammonium, pyrrolidinium, piperidinium, pyridinium, methylpyridinium, dimethylpyrdinium, trimethylpyridinium, N,N-dimethylaminopyridinium, 1,4-diazoniabicyclo[2.2.2]octane, and so on. Preferable examples of the phosphonium moieties are tetramethylphosphonium, tetraethylphosphonium, tetrapropylphosphonium, tetrabutylphosphonium, tetraphenylphosphonium, and so on. Among salts, alkali metal salts are most preferable because of cost and high yields of the products.

More preferable examples of the organic compounds are ketones, phenols, and their salts because of cost and availability. Salts of phenols are further preferable since the yields are high and the halogenated products are stable and not lachrymatory, since some of halogenated ketones are lachrymatory. Salts of alkylphenols such as each isomer of methylphenol (cresol), each isomer of dimethylphenol, each isomer of trimethylphenol, each isomer of ethylphenol, each isomer of n-propylphenol, each isomer of isopropylphenol, each isomer of n-butylphenol, each isomer of sec-butylphenol, each isomer of isobutylphenol, and each isomer of tert-butylphenol are furthermore preferable since the halogenated products are easily removed from the reaction mixture by extracting with a normal organic solvent. Among them, alkali metal salts of methylphenol and tert-butylphenol are more preferable because of cost, and alkali metal salts of 4-tert-butylphenol are most preferable since the halogenated products are more effectively removed because of fast and clear phase separation in addition to cost.

When one mole of a organic compound consumes n mole of halogen atoms from perfluoroalkanedi(sulfonyl halide) (formula IV), the amount of a target organic compound used with one mole of perfluoroalkanedi(sulfonyl halide) (formula IV) is from about 2/n mole to an amount in large excess of 5/n moles. From the viewpoint of cost, about 2/n to about 5/n moles of organic compound is preferable. Note that, in Example 1, one mole of an organic compound can consume 2 moles of halogen atoms (Br and/or Cl) (see step 3).

In some embodiments of step three, the reactions are carried out in a solvent, as the reaction can efficiently take place in a solvent. Preferable solvents will not substantially react with the starting materials and/or reagents, the intermediates, or the final products.

Suitable solvents for use herein include, but are not limited to, water; nitriles such as acetonitrile, propionitrile, butyronitrile, and so on; ethers such as diethyl ether, dipropyl ether, di(isopropyl)ether, dibutyl ether, tert-butyl methyl ether, tetrahydrofuran, dioxane, and so on; hydrocarbons such as pentane, hexane, heptane, octane, and so on; halocarbons such as dichloromethane, chloroform, carbon tetrachloride, dichloroethane, trichloroethane, trichlorotrifluoroethane, and so on; esters such as methyl acetate, ethyl acetate, methyl propionate, and so on; and mixtures of any two or more of the above. Water, a mixture of water and a halocarbon, and a mixture of water and a hydrocarbon are preferable solvents for the reaction of step three. These solvents typically provide higher product yield. Also note that water or a mixture of water and a halocarbon are more preferable when easy phase separation, cost, and yield are taken into consideration.

In order to get a good product yield, the preferable amount of solvent can be chosen in the range of about 0.1 L to about 10 L per 1 mol of the perfluoroalkanedi(sulfonyl halide). About 0.2 L to about 5 L of solvent is more preferable. When a mixture of two solvents is used, it is preferable that the ratio can be chosen in the range of about 5:95 to about 95:5, and more preferably in the range of about 1:9 to about 9:1.

In order to optimize yield with regard to step three, the reaction temperature is selected in the range of from about −30° C. to about +100° C. More typically, the reaction temperature is selected in the range of from about −20° C. to about +70° C. Most typically, the reaction temperature is selected in the range of from about −10° C. to about +50° C.

As described for step one, reaction times for step three vary dependent on reaction temperature, substrate type, reagent type, solvent type, and amounts used of each component. Therefore, reaction time is modified by reaction conditions.

An additional preferable embodiment of step three is that the organic layer obtained in step two is mixed with a solution of a target organic compound in water, and after the reaction is complete, the aqueous layer is separated away from the organic layer. The obtained aqueous layer contains perfluoroalkanedi(sulfinate) having formula (IV), which is used in step four.

Step 4 (Scheme 1)

Step four includes reacting the obtained perfluoroalkanedi (sulfinate) with chlorine ($Cl_2$) to form perfluoroalkanedi(sulfonyl chloride), as represented by formula (I).

In one embodiment of the invention, step four is carried out using a solvent. Typical solvents will not substantially react with a starting material, reagent(s), formed intermediates, or the final product(s). Suitable solvents include, but are not limited to, water; nitriles such as acetonitrile, propionitrile, butyronitrile, and so on; ethers such as diethyl ether, dipropyl ether, di(isopropyl)ether, dibutyl ether, tert-butyl methyl ether, tetrahydrofuran, dioxane, and so on; hydrocarbons such as pentane, hexane, heptane, octane, and so on; halocarbons such as dichloromethane, chloroform, carbon tetrachloride, dichloroethane, trichloroethane, trichlorotrifluoroethane, and so on; esters such as methyl acetate, ethyl acetate, methyl propionate, and so on; and a mixture of these.

Water, a mixture of water and a halocarbon, and a mixture of water and a hydrocarbon are preferable as a solvent for the reaction of step four. Solvents herein generally provide for higher yields of products. Water or a mixture of water and a halocarbon is a more preferable solvent from a viewpoint of easy phase separation, yield, and cost.

In order to get a good product yield, the preferable amount of solvent can be chosen in the range of about 0.1 L to about 10 L per 1 mol of perfluoroalkanedi(sulfinate) (formula IV) present. About 0.2 L to about 5 L of solvent is more preferable. When a mixture of two solvents is used, it is preferable that the ratio can be chosen in the range of about 5:95 to about 95:5, and more preferably in the range of about 1:9 to about 9:1. When the aqueous layer obtained in step 3 is used, no additional solvent is needed or some solvent may be added in order to be a suitable concentration of the perfluoroalkanedi(sulfinate) mentioned above.

In order to obtain good product yield, the amount of chlorine used can be selected in the range of from about 2 to about 5 moles per one mole of perfluoroalkanedi(sulfinate).

In order to obtain good yields of the products, the reaction temperature of step four can be selected in the range of −50° C.~+100° C. More preferably, the temperature can be selected in the range of −40° C.~+70° C. Furthermore preferably, the temperature can be selected in the range of −20° C.~+50° C.

As described for step one, reaction times for step four vary dependent on reaction temperature, substrate, solvent type, and amounts used of each component. Therefore, reaction time is modified by reaction conditions.

An additional preferable embodiment of step four is that the aqueous layer obtained by step three can be treated with a chlorine gas, and after the reaction is complete, the products are obtained by extracting with an organic solvent. The obtained extract is then concentrated and the products are isolated by normal procedures such as distillation or crystallization.

According to the present invention, highly pure and hydrogen atom-free perfluoroalkanedi(sulfonyl chloride) having the formula (I) can be easily and cost-effectively produced with low cost reagents. Steps one through four provide a simple isolation procedure allowing phase separation techniques to act as a platform for preparing cost effective, industrial amounts of perfluoroalkanedi(sulfonyl chloride). This is a significant improvement over the prior art.

Although the proceeding disclosure is broken into a reaction including four steps, the description is from the standpoint of convenience, other numbers of steps can be described as long as the above described reactions are performed in the order described herein.

The following examples will illustrate the present invention in more detail, but it should be understood that the present invention is not deemed to be limited thereto.

EXAMPLES

Example 1

Synthesis of perfluoropropane-1,3-di(sulfonyl-chloride) from 1,3-dibromoperfluoropropane

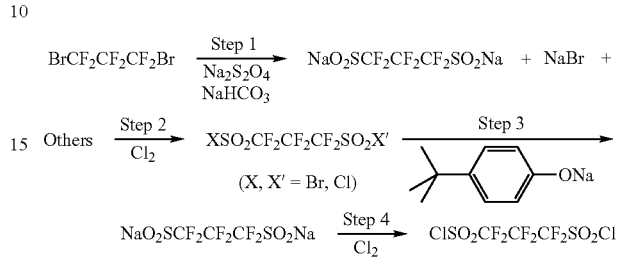

Step 1: Synthesis of sodium perfluoropropane-1,3-di(sulfinate) and NaBr

A 2 L three-necked round bottom flask equipped with a magnetic stirrer, a dropping funnel, and a condenser was charged with 188 g (1.08 mol, assay ca. 85%) sodium dithionite (sodium hydrosulfite) $Na_2S_2O_4$) and 121 g (1.44 mol) of sodium hydrogencarbonate. Nitrogen gas was flowed to remove air in the flask. Water (600 mL) and then acetonitrile (400 mL) were added to the mixture and the reaction mixture was warmed to 35° C. After the nitrogen flow was stopped, 124 g (0.400 mol) of 1,3-dibromoperfluoropropane (Exfluor Research Corp.) was dropwise added into the stirred reaction mixture for 2 hours. During dropping, gas evolution from the reaction mixture was observed. After dropping, the reaction mixture was kept at 35° C. for 0.5 hours and then heated to 50° C. After keeping the reaction at 50° C. for 1 hour, the reaction mixture was heated to 65° C. After keeping the reaction at 65° C. for 2 hours, gas evolution ceased. The reaction mixture was cooled to room temperature and transferred to a separatory funnel. The lower water layer was separated from the upper organic (acetonitrile) layer. In order to remove some acetonitrile which dissolved in the water layer, the water layer was concentrated until distillate no longer evolved from the water layer under pressure of 310 mmHg at bath temperature (65-75° C.), giving about 913 g of the water layer. $^{19}F$ NMR analysis (using hexafluoroglutaric acid as a reference) showed that the water layer contained 0.376 mol of sodium perfluoropropane-1,3-di(sulfinate). The yield was 94%. $^{19}F$-NMR (in $D_2O$); δ −122.8 (s, 2F), −129.7 (s, 4F) ppm.

It was reasonable that the water layer contained sodium bromide as another product of which yield was at least the same as that of the sodium perfluoropropane-1,3-di(sulfinate).

Step 2: Synthesis of perfluoropropane-1,3-di(sulfonyl halides)

The water layer (1113 g) containing sodium perfluoropropane-1,3-di(sulfinate) (0.341 mol) and NaBr, obtained according to Step 1, was charged into a 2 L three-necked round bottom flask equipped with a mechanical stirrer, a thermocouple, and a gas inlet and outlet. While nitrogen gas was flowed through the flask, the stirred reaction solution was cooled to below 0° C. in a bath of −5° C. After the nitrogen flow was stopped, chlorine gas (Cl$_2$) was introduced into the reaction solution at a flow rate of 230 ml/min until the absorption of chlorine ceased. The total flowed amount of chlorine was 45,850 mL (2.05 moles). Nitrogen gas was then flowed for 30 min through the solution to remove excess chlorine. Dichloromethane (600 mL) and some water were added to the reaction mixture, which was then stirred. On standing, the mixture separated into two layers. The lower organic (dichloromethane) layer was separated from the upper aqueous or water layer. $^{19}$F NMR analysis showed that the organic layer contained perfluoropropane-1,3-di(sulfonyl bromide), BrSO$_2$CF$_2$CF$_2$CF$_2$SO$_2$Br, 1-(bromosulfonyl)-3-(chlorosulfonyl)perfluoropropane, BrSO$_2$CF$_2$CF$_2$CF$_2$SO$_2$Cl, and perfluoropropane-1,3-di(sulfonyl chloride), ClSO$_2$CF$_2$CF$_2$CF$_2$SO$_2$Cl, in a ratio of 82:8:10 and the total yield of the perfluoropropane-1,3-di(sulfonyl halides) was 95%. The data of $^{19}$F-NMR δ (in acetonitrile-d$_3$) are as follows: BrSO$_2$CF$_2$CF$_2$CF$_2$SO$_2$Br: −105.10 (s, 4F, CF$_2$S), −117.70 (s, 2F, CF$_2$) ppm: BrSO$_2$CF$_2$CF$_2$CF$_2$SO$_2$Cl; −105.10 (s, 4F, CF$_2$S), −117.58 (s, 2F, CF$_2$) ppm: ClSO$_2$CF$_2$CF$_2$CF$_2$SO$_2$Cl; −105.10 (s, 4F, CF$_2$S), −117.46 (s, 2F, CF$_2$) ppm.

Step 3: Synthesis of sodium perfluoropropane-1,3-di(sulfinate)

4-tert-Butylphenol (98 g, 0.650 mol) was charged into a 2 L three-necked round bottom flask equipped with a mechanical stirrer, a dropping funnel, and a condenser. The flask was purged with nitrogen gas and a solution of 26.7 g of sodium hydroxide (0.650 mol) in 820 mL of water was added to the flask. The stirred reaction mixture was heated at 50° C. until 4-tert-butylphenol was completely dissolved. In this way, 4-tert-butylphenol was reacted with sodium hydroxide to form sodium 4-tert-butylphenolate. The solution of sodium 4-tert-butylphenolate in water was then cooled to 20° C. and 350 mL of dichloromethane was added to the solution. The organic layer obtained in step two, which contained 0.325 mol of the perfluoropropane-1,3-di(sulfonyl halides), was dropwise added to the reaction mixture for 2 hours under nitrogen atmosphere. The reaction mixture was stirred at 20° C. for 12 hours and transferred to a separatory funnel. The upper water layer was separated from the lower organic (dichloromethane) layer. The water layer was then washed by 300 mL of ethyl acetate. The water layer was 953 g. $^{19}$F-NMR analysis (using hexafluoroglutaric acid as a reference) showed that the water layer contained 0.295 mol of sodium perfluoropropane-1,3-di(sulfinate). The yield was 91%. $^{19}$F-NMR (in D$_2$O); δ −122.9 (s, 2F, CF$_2$), −129.8 (s, 4F, CF$_2$S) ppm.

The lower organic layer was analyzed by CC/Mass spectrometry and found to include the compounds (i)~(v) with a ratio of 31:32:25:6:6=(i):(ii):(iii):(iv):(v).

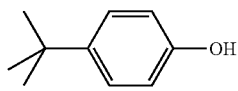

(i)

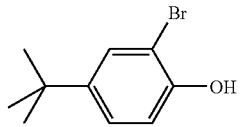

(ii)

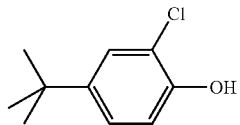

(iii)

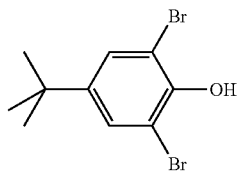

(iv)

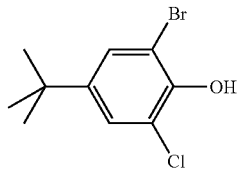

(v)

Step 4: Synthesis of perfluoropropane-1,3-di(sulfonyl chloride)

A 2 L three-necked round bottom flask equipped with a mechanical stirrer, a thermocouple, and a gas inlet and outlet was charged with 953 g of the water layer obtained in step three, which contained 0.295 mole of the sodium perfluoropropane-1,3-di(sulfinate). While nitrogen gas was flowed through the flask, the solution was cooled to below 0° C. in a bath at −5° C. After nitrogen flow was stopped, chlorine gas was introduced into the reaction solution at a flow rate of 120 mL/min until the absorption of chlorine ceased. The total introduced amount of chlorine was 13,300 mL (0.594 mol). Nitrogen gas was then flowed through the reaction mixture for 30 minutes to remove an excess of chlorine. Into the reaction mixture was added 300 mL of dichloromethane and the mixture was stirred. On standing, the reaction mixture separated into two layers. The lower organic (dichloromethane) layer was separated from the upper aqueous or water layer and dried over anhydrous magnesium sulfate. After filtration, the filtrate was concentrated under reduced pressure. The residue was distilled under reduced pressure to give 92 g of perfluoropropane-1,3-di(sulfonyl chloride). The yield was 90%. The boiling point, melting point, and spectral data are shown in the following: B.p. 72-75° C./10 mmHg: Melting point: 44-45.5° C.: $^{19}$F-NMR (in acetonitrile-d$_3$); δ −105.16 (s, 4F, CF$_2$S), −117.45 (s, 2F, CF$_2$) ppm.

Perfluoropropane-1,3-di(sulfonyl chloride) was prepared in a total 73% yield from 1,3-dibromoperfluoropropane by Steps 1, 2, 3, and 4. This is significant in that perfluoropropane-1,3-di(sulfonyl chloride) was produced from BrCF$_2$CF$_2$CF$_2$Br, which can be provided as highly pure and hydrogen atom-free material, in high yield with easy phase separation techniques and low cost.

Example 2

Synthesis of perfluoropropane-1,3-di(sulfonyl chloride) from 1,3-dibromoperfluoropropane Step 1: Synthesis of sodium perfluoropropane-1,3-di(sulfinate) and NaBr using $Na_2HPO_4$ instead of $NaHCO_3$ used in Step 1 of Example 1

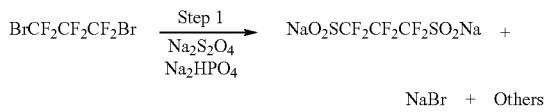

A 500 mL three-necked round bottom flask was charged with 39.7 g (0.228 mol, assay ca. 85%) sodium dithionite (sodium hydrosulfite) and 32.4 g (0.228 mol) of sodium phosphate dibasic ($Na_2HPO_4$). Nitrogen gas was flowed to remove air in the flask, and 150 mL of water and then 100 mL of acetonitrile were added to the flask. The reaction mixture was heated to 35° C. Into the stirred mixture, 30 g (0.097 mol) of 1,3-dibromoperfluoropropane was added dropwise over 0.5 hour. After dropping, the reaction mixture was kept at 35° C. for 0.5 hour, and then heated to 50° C. The reaction mixture was kept at 50° C. for 0.5 hour, and then heated to 65° C. The mixture was continuously stirred at 65° C. overnight. The reaction mixture was then cooled to room temperature and transferred into a separatory funnel. The lower water layer was separated from the upper organic layer. The obtained water layer was 313 g. $^{19}F$-NMR analysis showed that the water layer contained 0.081 mol of sodium perfluoropropane-1,3-di(sulfinate). The yield was 84%. $^{19}F$-NMR (in $D_2O$). δ −122.76 (s, 2F, $CF_2$), −129.69 (s, 4F, $CF_2S$) ppm.

For step 2 below, the water layer may optionally be concentrated under reduced pressure to remove some acetonitrile contained in the water layer.

Steps 2, 3, and 4

The water layer obtained in step 1 may be treated successively by Steps 2, 3, and 4 in the same way as shown in Example 1, giving perfluoropropane-1,3-di(sulfonyl chloride) in good yield.

Example 3

Synthesis of perfluoropropane-1,3-di(sulfonyl bromide) from sodium perfluoropropane-1,3-di(sulfinate) with bromine

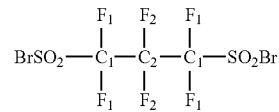

A water layer containing perfluoropropane-1,3-di(sulfinate) was prepared from 1,3-dibromoperfluoropropane according to the procedure of Step 1 or Steps 1, 2, and 3 of Example 1. The water layer (122 g) containing 0.038 moles of sodium perfluoropropane-1,3-di(sulfinate), which was prepared by the procedure of Steps 1, 2, and 3, was charged into a three-necked round bottom flask equipped with a mechanical stirrer, a dropping funnel, and a gas inlet and outlet. Into the flask, 100 mL of dichloromethane was added. After the flask was purged with nitrogen gas, the reaction mixture was cooled in a bath of −5° C. Bromine was dropwise added to the stirred reaction mixture until a red color remained in the solution. The amount of bromine used was 6.5 mL (0.126 mol). The reaction mixture was kept at −5° C. for 20 minutes with stirring. The red reaction mixture was transferred into a separatory funnel. The lower organic (dichloromethane) layer was separated from the upper water layer and dried over anhydrous magnesium sulfate. After filtration, the filtrate was evaporated under reduced pressure to give a crystalline solid of perfluoropropane-1,3-di(sulfonyl bromide). The crystalline solid weighed 15.6 g (94% yield). It was further purified by recrystallization from n-pentane at −20° C. to give colorless needle crystals. The physical and spectral data of perfluoropropane-1,3-di(sulfonyl bromide) is shown in the following:

Melting point: 45-46° C.

$^{19}F$-NMR (in acetonitrile-$d_3$); δ −105.07 (s, 4F, $CF_2S$), −117.70 (s, 2F, $CF_2$) ppm:

$^{13}C$-NMR (in $CDCl_3$): δ 110.31 (triplet-quintet, $J_{C_2-F_2}$=267.1 Hz, $J_{C_2-F_2}$=30.7 Hz), 113.13 ppm (triplet-triplet, $J_{C_1-F_1}$=316.1 Hz, $J_{C_1-F_2}$=36.1 Hz), Chemical structure of perfluoropropane-1,3-di(sulfonyl bromide)

$$BrSO_2-\underset{\underset{F_1}{|}}{\overset{\overset{F_1}{|}}{C_1}}-\underset{\underset{F_2}{|}}{\overset{\overset{F_2}{|}}{C_2}}-\underset{\underset{F_1}{|}}{\overset{\overset{F_1}{|}}{C_1}}-SO_2Br$$

Example 4

Synthesis of perfluorobutane-1,4-di(sulfonyl chloride) from 1,4-dibromoperfluorobutane

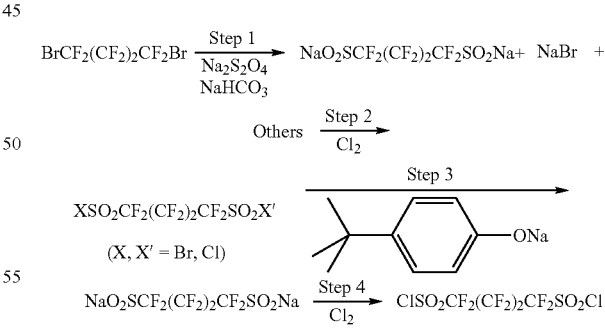

Step 1: Synthesis of sodium perfluorobutane-1,4-di(sulfinate) and NaBr

A 1 L three-necked round bottom flask equipped with a magnetic stirrer, a dropping funnel, and a condenser was charged with 47.1 g (0.271 mol, assay ca. 85%) of sodium dithionite (sodium hydrosulfite) ($Na_2S_2O_4$) and 30.2 g (0.360 mol) of sodium hydrogencarbonate. Nitrogen gas was flowed to remove air in the flask. Water (150 mL) and then acetonitrile (100 mL) were added into the mixture and the reaction mixture was warmed to 35° C. After the nitrogen flow was stopped, 36.0 g (0.100 mol) of 1,4-dibromoperfluorobutane (Exfluor Research Corp.) was dropwise added into the stirred reaction mixture over a period of two hours. During dropping, a gas evolution from the reaction mixture was observed. After dropping, the reaction mixture was kept at 35° C. for 0.5 hour and then heated to 50° C. The reaction was maintained at 50° C. for 2 hours and then heated to 65° C. After keeping the reaction at 65° C. for 1.5 hours, gas evolution ceased. The reaction mixture was next cooled to room temperature and transferred to a separatory funnel. The lower water layer was separated from the upper organic (acetonitrile) layer using an additional 100 mL of water. In order to remove some acetonitrile dissolved in the water layer, the water layer was concentrated under pressure of 260 mmHg on a bath of 70° C. until the water layer became a clear solution, giving about 335 g of the water layer. $^{19}$F NMR analysis (using hexafluoroglutaric acid as a reference) showed that the water layer contained 0.086 mol of sodium perfluorobutane-1,3-di(sulfinate). The yield of sodium perfluorobutane-1,3-di (sulfinate) was 86%. $^{19}$F-NMR (in D$_2$O); δ −122.51 (s, 4F, CF$_2$), −130.03 (s, 4F, CF$_2$) ppm. It was reasonable that the water layer contained sodium bromide as another product, the yield of which was at least the same as that of the sodium perfluorobutane-1,4-di(sulfinate).

Step 2: Synthesis of perfluorobutane-1,4-di(sulfonyl halides)

The water layer (335 g) containing 0.086 mol of sodium perfluorobutane-1,4-di(sulfinate), obtained by Step 1 above, was charged into a 2 L three-necked round bottom flask equipped with a mechanical stirrer, a thermocouple, and a gas inlet and outlet. While nitrogen gas was flowed through the flask, the stirred reaction solution was cooled to below 0° C. on a bath of −5° C. After the nitrogen flow was stopped, chlorine gas (Cl$_2$) was introduced into the reaction solution at a flow rate of 64 mL/min until the absorption of chlorine ceased. The total flowed amount of chlorine was 11,670 mL (0.521 mol). After nitrogen gas was flowed to remove an excess of chlorine, dichloromethane (600 mL) and water (230 mL) were added to the reaction mixture, which was then stirred. On standing, the mixture was separated to two layers. The lower organic layer was separated from the upper water layer. $^{19}$F NMR analysis showed that the organic layer contained perfluorobutane-1,4-di(sulfonyl bromide), BrSO$_2$CF$_2$(CF$_2$)$_2$CF$_2$SO$_2$Br, and perfluorobutane-1,4-di(sulfonyl chloride), ClSO$_2$CF$_2$(CF$_2$)$_2$CF$_2$SO$_2$Cl, in a ratio of 72:28 and the total yield of these perfluorobutane-1,4-di(sulfonyl halides) was 92%. The data of $^{19}$F-NMR δ (in acetonitrile-d$_3$) were as follows: BrSO$_2$CF$_2$(CF$_2$)$_2$CF$_2$SO$_2$Br: −105.07 (s, 4F, CF$_2$), −119.48 (s, 4F, CF$_2$) ppm: ClSO$_2$CF$_2$(CF$_2$)$_2$CF$_2$SO$_2$Cl; −105.07 (s, 4F, CF$_2$), −119.36 (s, 4F, CF$_2$) ppm. 1-(Bromosulfonyl)-4-(chlorosulfonyl)perfluorobutane, BrSO$_2$CF$_2$(CF$_2$)$_2$CF$_2$SO$_2$Cl, could not be observed in $^{19}$F-NMR spectra probably due to overlapping of the signals by the other products.

Step 3: Synthesis of sodium perfluorobutane-1,4-di(sulfinate)

4-tert-Butylphenol (27.6 g, 0.184 mol) was charged into 2 L three-necked round bottom flask equipped with a mechanical stirrer, a dropping funnel, and a condenser. The flask was purged with nitrogen gas, and 184 mL of 1N aqueous sodium hydroxide solution added to the flask. Additionally, 47 mL of water was added into the solution. The stirred reaction mixture was heated at 50° C. until 4-tert-butylphenol was completely dissolved. In this way, 4-tert-butylphenol was reacted with sodium hydroxide to form sodium 4-tert-butylphenolate. The solution of sodium 4-tert-butylphenolate in water was then cooled to 20° C. and 100 mL of dichloromethane added to the solution. The organic layer obtained in step 2, which contained 0.0835 mole of the perfluorobutane-1,4-di (sulfonyl halides), was dropwise added to the reaction mixture for 2 hours. The reaction mixture was stirred at 20° C. for 12 hours and transferred to a separatory funnel. The upper water layer was separated from the lower organic (dichloromethane) layer. The water layer was then washed using 100 mL of ethyl acetate. The water layer was 274 g. $^{19}$F-NMR analysis (using hexafluoroglutaric acid as a reference) showed that the water layer contained 0.068 mol of sodium perfluorobutane-1,4-di(sulfinate). The yield was 81%. $^{19}$F-NMR (in D$_2$O); δ −122.67 (s, 4F, CF$_2$), −130.12 (s, 4F, CF$_2$) ppm.

Step 4: Synthesis of perfluorobutane-1,4-di(sulfonyl chloride)

A 500 mL three-necked round bottom flask equipped with a mechanical stirrer, a thermocouple, and a gas inlet and outlet was charged with 68 g of the water layer obtained in step 3 above, which contained 0.0168 mole of sodium perfluorobutane-1,4-di(sulfinate). Dichloromethane (50 mL) was added to the water layer. While nitrogen gas was flowed through the flask, the solution was cooled to below 0° C. using a −5° C. bath. After nitrogen flow was stopped, chlorine gas was introduced into the reaction solution at a flow rate of 30 mL/min until the absorption of chlorine ceased. The total introduced amount of chlorine was 1,030 mL (0.0461 mol). Nitrogen gas was then flowed through the reaction mixture for 30 minutes to remove an excess of chlorine. The reaction mixture was transferred to a separatory funnel. The lower organic (dichloromethane) layer was separated from the upper water layer and dried over anhydrous magnesium sulfate. After filtration, the filtrate was evaporated under reduced pressure to give a crystalline solid of perfluorobutane-1,4-di(sulfonyl chloride). The perfluorobutane-1,4-di(sulfonyl chloride) weighted 6.1 g and the yield was 91%. It was further purified by distillation. Boiling point; 60-65° C./2 mmHg; melting point: 46-47° C.: $^{19}$F-NMR (in acetonitrile-d$_3$); δ −105.16 (s, 4F, CF$_2$), −119.36 (s, 4F, CF$_2$) ppm.

Perfluorobutane-1,4-di(sulfonyl chloride) was prepared having a total 58% yield from 1,4-dibromoperfluorobutane by Steps 1, 2, 3, and 4.

Example 5

Synthesis of perfluorobutane-1,4-di(sulfonyl bromide) from sodium perfluorobutane-1,4-di(sulfinate) with bromine $$NaO_2SCF_2(CF_2)_2CF_2SO_2Na \xrightarrow[\text{in water/CH}_2\text{Cl}_2]{Br_2} BrSO_2CF_2(CF_2)_2CF_2SO_2Br$$

A water layer containing sodium perfluorobutane-1,4-di (sulfinate) was prepared from 1,4-dibromoperfluorobutane according to the procedure of Step 1 or Steps 1, 2, and 3 in Example 4. The water layer (70 g) containing 0.017 mol of the perfluorobutane-1,4-di(sulfinate), prepared by the procedure of Steps 1, 2, and 3, was charged into a three-necked round bottom flask equipped with a mechanical stirrer, a dropping funnel and a gas inlet and outlet. Into the water layer, 50 mL of dichloromethane was added. After the flask was purged with nitrogen gas, the reaction mixture was cooled on a −5° C. bath. Bromine ($Br_2$) was dropwise added to the stirred reaction mixture until a red color remained in the solution. The amount of bromine added was 2.7 mL (0.052 mol). The reaction mixture was kept at −5° C. for 30 minutes with stirring. The red reaction mixture was transferred into a separatory funnel. The lower organic (dichloromethane) layer was separated from the upper water layer and dried over anhydrous magnesium sulfate. After filtration, the filtrate was evaporated under reduced pressure to give a crystalline solid of perfluorobutane-1,4-di(sulfonyl bromide). The perfluorobutane-1,4-di(sulfonyl bromide) weighed 8.3 g (98% yield). It was further purified by recrystallization from a mixture of dichloromethane and n-pentane at −20° C. to give colorless needle crystals. The physical and spectral data of perfluorobutane-1,4-di(sulfonyl bromide) are shown in the following:

Melting point: 86.5-88° C.

$^{19}$F-NMR (in acetonitrile-$d_3$); δ −105.07 (s, 4F, $F_1$), −119.48 (s, 4F, $F_2$) ppm.

$^{13}$C-NMR (in $CDCl_3$): δ 110.43 (triplet-quintet, $J_{C_2-F_2}$=276.4 Hz, $J_{C_2-F_1}$=32.8 Hz), 113.18 ppm (triplet-triplet, $J_{C_1-F_1}$=314.6 Hz, $J_{C_1-F_2}$=34.7 Hz).

Chemical structure of perfluorobutane-1,4-di(sulfonyl bromide):

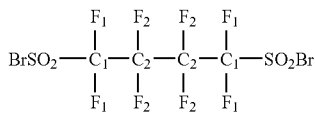

Example 6

Synthesis of perfluoropropane-1,3-di(sulfonyl chloride) from 1,3-dibromoperfluoropropane

Steps 1 and 2

1,3-Dibromoperfluoropropane was treated in the same manner as in Steps 1 and 2 of Example 1.

Step 3: Synthesis of sodium perfluoropropane-1,3-di(sulfinate) by reaction of perfluoropropane-1,3-di(sulfonyl halides) with sodium 4-methylphenolate

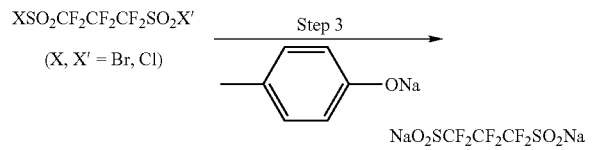

p-Cresol (4-methylphenol) (1.09 g, 0.010 mol) was charged into a three-necked round bottom flask. The flask was purged with nitrogen gas, and 10.1 mL of 1N aqueous sodium hydroxide solution added to the flask. The reaction mixture was stirred at room temperature. p-Cresol was completely dissolved, in this way, p-cresol was reacted with sodium hydroxide to form sodium 4-methylphenolate. 10 mL of dichloromethane was added to the solution and then the organic (dichloromethane) layer (10 mL) obtained in step 2 above was dropwise to the solution over 15 min. The organic layer contained 4.6 mmol of the perfluoropropane-1,3-di(sulfonyl halides). The reaction mixture was stirred at room temperature for 2 hours and transferred to a separatory funnel. The upper water layer was separated from the lower organic (dichloromethane) layer. The water layer was then washed with 20 mL of ethyl acetate. The water layer was 20.6 g. $^{19}$F-NMR analysis (using hexafluoroglutaric acid as a reference) showed that the water layer contained 3.8 mmol of sodium perfluoropropane-1,3-di(sulfinate). The yield was 83%. $^{19}$F-NMR (in $D_2O$); δ −122.9 (s, 2F, $CF_2$), −129.8 (s, 4F, $CF_2S$) ppm.

Step 4

The sodium perfluoropropane-1,3-di(sulfinate) obtained by Step 3 may be treated in the same way as in Step 4, Example 1, giving perfluoropropane-1,3-di(sulfonyl chloride) in good yield.

Example 7

Synthesis of perfluoropropane-1,3-di(sulfonyl chloride) from 1,3-dibromoperfluoropropane

Steps 1 and 2

1,3-Dibromoperfluoropropane was treated in the same manner as in Steps 1 and 2 in Example 1.

Step 3: Preparation of sodium perfluoropropane-1,3-di(sulfinate) by reaction of perfluoropropane-1,3-di(sulfonyl halides) with acetone/NaOH

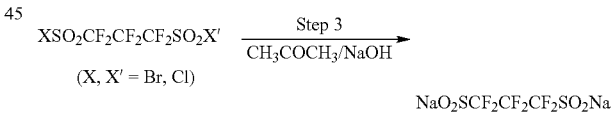

Acetone (1.14 g, 0.01995 mol) was charged into a three-necked round bottom flask. After the flask was purged with nitrogen gas, 19.5 mL of 1N aqueous sodium hydroxide solution and then 10 mL of water added to the flask. The reaction mixture was stirred at room temperature. Into the solution, 10 mL of dichloromethane was added and then the organic (dichloromethane) layer (10 mL) obtained in the step 2 above, which contained 8.89 mmol of the perfluoropropane-1,3-di (sulfonyl halides), was dropwise added for 15 min. The reaction mixture was stirred at room temperature for 2 hours and transferred to a separatory funnel. The upper water layer was separated from the lower organic (dichloromethane) layer. The water layer was then washed twice with 30 mL of dichloromethane. The water layer was 31.6 g. $^{19}$F-NMR analysis (using hexafluoroglutaric acid as a reference) showed that the water layer contained 6.38 mmol of sodium perfluoropropane-1,3-di(sulfinate). The yield was 72%. $^{19}$F-NMR (in D$_2$O); δ −122.9 (s, 2F, CF$_2$), −129.8 (s, 4F, CF$_2$S) ppm.

Step 4

The sodium perfluoropropane-1,3-di(sulfinate) obtained in Step 3 may be treated in the same was as in Step 4, Example 1, giving perfluoropropane-1,3-di(sulfonyl chloride) in good yield.

It will be clear that the invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims. All publications cited herein are hereby incorporated by reference.

What is claimed is:

1. A method for preparing a perfluoroalkanedi(sulfonyl chloride) having a formula (I) as follows:

ClSO$_2$CF$_2$(CF$_2$)$_n$CF$_2$SO$_2$Cl  (I)

the method comprising:
a first step of reacting a dibromoperfluoroalkane having a formula (II):

BrCF$_2$(CF$_2$)$_n$CF$_2$Br  (II)

with SO$_2$ radical anion or a source of SO$_2$ radical anion;
a second step of reacting the reaction mixture obtained in step one with a halogen selected from a group consisting of chlorine (Cl$_2$), bromine (Br$_2$), and interhalogen compounds consisting of chlorine atom and bromine atom, to form a perfluoroalkanedi(sulfonyl halide) having a formula (III):

XSO$_2$CF$_2$(CF$_2$)$_n$CF$_2$SO$_2$X'  (III);

a third step of reacting the obtained perfluoroalkanedi(sulfonyl halide) with an organic compound to form a perfluoroalkanedi(sulfinate) having a formula (IV):

MO$_2$SCF$_2$(CF$_2$)$_n$CF$_2$SO$_2$M  (IV);

and a fourth step of reacting the perfluoroalkanedi(sulfinate) with chlorine (Cl$_2$) to form perfluoroalkanedi(sulfonyl chloride);
in which: n is a whole number from one to eight, X and X' are independently a bromine atom or a chlorine atom, and M is a hydrogen atom, a metal atom, an ammonium moiety, or a phosphonium moiety.

2. The method of claim 1 wherein a source of SO$_2$ radical anion is sodium dithionite (Na$_2$S$_2$O$_4$).

3. The method of claim 1 further comprising performing the first step in a solvent wherein the solvent is a mixture of water and acetonitrile.

4. The method of claim 3, wherein, after the reaction of the first step, an aqueous layer is separated from the organic layer and used in step two.

5. The method of claim 4, wherein the acetonitrile dissolved in the aqueous layer is at least partially removed from the aqueous layer and the resulting aqueous layer is used in step two.

6. The method of claim 1 wherein the halogen used in step two is chlorine (Cl$_2$).

7. The method wherein the reaction mixture used in step two is the aqueous layer obtained according to claim 4.

8. The method wherein the reaction mixture used in step two is the resulting aqueous layer obtained according to claim 5.

9. The method of claim 1 further comprising separating an organic layer from an aqueous layer after the reaction of the second step and using the organic layer in the third step.

10. The method of claim 1 wherein the organic compound used in step three is selected from a group consisting of ketones, phenols, and salts thereof.

11. The method of claim 1 wherein the organic compound used in step three is selected from a group consisting of alkylphenols and salts thereof.

12. The method of claim 1 wherein the organic compound used in step three is an alkali metal salt of 4-tert-butylphenol.

13. The method of claim 1 wherein the third step further comprises performing the reaction in a solvent wherein the solvent is water or a mixture of water and a halocarbon.

14. The method of claim 1 further comprising separating the aqueous layer from the organic layer after the reaction of the third step and using the aqueous layer in the fourth step.

15. The method wherein the fourth step comprises reacting the aqueous layer obtained according to claim 14 with chlorine (Cl$_2$).

16. Perfluoroalkanedi(sulfonyl bromide) having a formula (V):

BrSO$_2$CF$_2$(CF$_2$)$_n$CF$_2$SO$_2$Br  (V)

in which n is a whole number of one to eight.

17. Perfluoropropane-1,3-di(sulfonyl bromide).

18. Perfluorobutane-1,4-di(sulfonyl bromide).

* * * * *